(12) United States Patent
Adeyeye et al.

(10) Patent No.: US 8,679,511 B2
(45) Date of Patent: Mar. 25, 2014

(54) IN-SITU GEL OPHTHALMIC DRUG DELIVERY SYSTEM OF ESTRADIOL OR OTHER ESTROGEN FOR PREVENTION OF CATARACTS

(75) Inventors: Moji Christianah Adeyeye, Schaumburg, IL (US); Vicki L. Davis, Butler, PA (US); Uday K. Kotreka, Pittsburgh, PA (US)

(73) Assignee: Duquesne University of the Holy Spririt, Pittsburgh, PA (US)

( * ) Notice: Subject to any disclaimer, the term of this patent is extended or adjusted under 35 U.S.C. 154(b) by 364 days.

(21) Appl. No.: 12/924,495

(22) Filed: Sep. 28, 2010

(65) Prior Publication Data
US 2011/0082128 A1 Apr. 7, 2011

Related U.S. Application Data

(60) Provisional application No. 61/277,933, filed on Oct. 1, 2009.

(51) Int. Cl.
*A61K 9/00* (2006.01)
(52) U.S. Cl.
USPC .......................... 424/400; 514/912
(58) Field of Classification Search
USPC .......................... 424/400; 514/912
See application file for complete search history.

(56) References Cited

U.S. PATENT DOCUMENTS

| | | | | |
|---|---|---|---|---|
| 4,642,305 | A | * | 2/1987 | Johansson et al. ............ 514/182 |
| 4,861,760 | A | * | 8/1989 | Mazuel et al. .................. 514/54 |
| 2002/0107238 | A1 | * | 8/2002 | Bandyopadhyay et al. ....................... 514/211.15 |

OTHER PUBLICATIONS

Rowe et al., Handbook of Pharmaceutical Excipients-Sorbic Acid, Pharmaceutical Press, 2006, 5th Edition, 710-712.*
Banin et al., Chelator-Induced Dispersal and Killing of *Pseudomonas aeruginosa* Cells in a Biofilm, Appl Environ Microbiol. Mar. 2006; 72(3), printed from http://www.ncbi.nlm.nih.gov/pubmed/16517655?dopt=Abstract, Abstract only, 2 pages.*
Jarvis et al., The mechanism of carbonate killing of *Escherichia coli*, Lett Appl Microbiol. Sep. 2001;33(3), printed from http://www.ncbi.nlm.nih.gov/pubmed/11555203, Abstract only, 1 page.*
Stratford, M. et al., "Evidence that Sorbic Acid . . . ," Letters in Applied Microbiology, vol. 27, pp. 203-206 (1998).
Hales, Angela M. et al., "Estrogen Protects . . . ," J. Exp. Med, vol. 185, No. 2, pp. 273-280 (1997).
Annual Progress Report: 2006 Formula Grant, posted to Pennsylvania Department of Health Internet Web Site on Dec. 3, 2007.

* cited by examiner

*Primary Examiner* — Gigi Huang
(74) *Attorney, Agent, or Firm* — Barbara E. Johnson, Esq.

(57) ABSTRACT

An in-situ gel ophthalmic drug delivery system for estrogen containing an estrogen, a solubilizing and complexing agent, a humectant, a sorbic acid or sorbic acid based stabilizer, an optional chelating agent and gellan gum in the amount of about 0.1-0.5% w/v, optionally 0.1-0.3% w/v, of the composition.

10 Claims, No Drawings

IN-SITU GEL OPHTHALMIC DRUG DELIVERY SYSTEM OF ESTRADIOL OR OTHER ESTROGEN FOR PREVENTION OF CATARACTS

CROSS-REFERENCE TO RELATED APPLICATIONS

This patent application claims priority to, and incorporates herein by reference, U.S. Provisional Patent Application Ser. No. 61/277,933 filed Oct. 1, 2009, entitled, "In-Situ Ophthalmic Drug Delivery System of Estradiol or Other Estrogen for Prevention of Cataracts."

BACKGROUND OF THE INVENTION

1. Field of the Invention

The invention relates to ophthalmic drug delivery systems for reducing the incidence or severity of, or for preventing, cataracts.

2. Description of Related Art

The idea of using estrogen to protect lenses of the eye from cataract formation was published at least as early as 1997, in Hales, A., et al., "Estrogen Protects Lenses against Cataract Induced by Transforming Growth Factor-β (TGFβ)," *J. Exp. Med.*, The Rockefeller University Press, Vol. 185, pp. 273-280, January 1997. There have been many previous attempts to prepare a delivery system to introduce estrogen into the eye to attempt to reduce cataract formation. Prior attempts have been plagued with problems including but not limited to poor shelf stability; inadequate microbiostatic characteristics; inadequate delivery and bioavailability; and formulation difficulties due to the hydrophobic character of estrogen compounds and the particularly sensitive nature of eye tissues and eye fluid tolerances.

The high risk of cataracts in women is believed to be due to the sharp decline in estrogen levels that occur after menopause, although men experience cataracts also. Exposure to estrogen has been determined in human and animal studies to be protective by reducing the risk of cataracts. Although clinical and preclinical studies suggest that systemically administered estrogen therapy may reduce the risk of cataracts, many women are concerned about taking systemic estrogen treatments for fear of increasing other risks, especially breast cancer. Moreover, men who wish to avoid cataracts generally find the idea of systemic estrogen unacceptable. Ophthalmic administration (conjunctival sac instillation) of estrogen would eliminate the disadvantages of systemic administration including those mentioned above and also avoid the unwanted hepatic first-pass effect.

The concept of preparing an ophthalmic drug delivery system for estrogen is thus straightforward in itself, although it has heretofore posed an implementation challenge. In situ gel forming pharmaceuticals for eye instillation face an inherent paradox during their design phases. Engineering a liquid that will have low enough viscosity to make a good dropwise eye product that can still quickly form a gel in the eye is a conundrum to begin with, and then making such a quick-change composition shelf-stable, sterile and adequately antibacterial adds an additional challenge, not to mention identifying an overall medium compatible with the active agent to be delivered. For example, eye-compatible gel forming agents are most beneficially chosen from among amino acid or saccharide polymers, to avoid toxicity, and yet these constituents are themselves intrinsically likely to foster unacceptable growth of unwanted bacteria or other microbes in the eye. The chemical reactivities of a particular active agent require specialized engineering of the carrier to assure the gel-forming carrier is completely inert to the drug. The present invention overcomes all these challenges in presenting a new and surprisingly useful formula for delivering at least one estrogen topically to the eye, to treat cataracts already formed or forming or to reduce the incidence of cataract formation when topical treatment is provided to a healthy human eye. In particular, ophthalmic delivery of estrogen has to overcome several difficulties such as wastage of drug by rapid naso-lachrymal drainage, increased tear turnover upon instillation of the formulation and inherent physicochemical properties of the drug molecules, and particularly the troublesome hydrophobicity of estrogen as well as the extremely sensitive nature overall of the eye. As a paramount consideration, not only must the ophthalmic composition be safe and effective in the eye, but it must not create even the slightest discomfort or blurred vision or any other feature that the patient might find unacceptable, both to avoid eye damage and to maximize patient compliance.

SUMMARY OF THE INVENTION

In order to overcome all these enumerated challenges, the invention is an in-situ gel ophthalmic drug delivery system containing key constituents in key amounts in order to achieve all the necessary characteristics of eye safety, eye compatibility, product shelf-life, product sterility, and desired drug delivery of estrogen to the eye and especially to the lens. The in-situ gel ophthalmic drug delivery system is a shelf stable solution containing: sterile deionized water; 0.01-0.025% w/v of an estrogen compound (such as without limitation 17β-estradiol, ethinyl estradiol, estrone or estriol), preferably 0.005-0.025% w/v of an estrogen compound (such as without limitation 17β-estradiol, ethinyl estradiol, estrone or estriol), and more preferably about 0.025% w/v estradiol; 0.04-4% w/v of an agent capable of solubilizing and complexing estrogen compounds, such as either 0.5-2% w/v nonionic surfactant polysorbate (a well known nonionic surfactant and emulsifier derived from polyethoxylated sorbitan and oleic acid sometimes known as polysorbate 80 or TWEEN) or 0.06-0.6% w/v cyclodextrin, or preferably about 1-2% w/v polysorbate or more preferably about 1.6% w/v polysorbate; optional 2-3% w/v glycerin or more preferably 4-5% w/v mannitol, most preferably 5% w/v mannitol; 0.1-0.4% w/v (preferably 0.2-0.3% w/v) sorbic acid or potassium, calcium or sodium sorbate as preservative, most preferably about 0.3% w/v potassium sorbate; optionally about 0.01-0.03% w/v ethylenediamine tetraacetic acid (EDTA) or disodium edetate dihydrate, although preferably at least about 0.01-0.02% w/v ethylenediamine tetraacetic acid (EDTA) or disodium edetate dihydrate and most preferably about 0.02-0.03% w/v ethylenediamine tetraacetic acid (EDTA) or disodium edetate dihydrate; and gellan gum 0.1-0.5% w/v, preferably about 0.1-0.3% w/v, most preferably about 0.3% w/v as an in-situ gel forming polymer vehicle. These components in these combinations and amounts surprisingly solve the heretofore encountered problems of excipient incompatibility, shelf instability, and inadequate sterility due to preservative incompatibility, while still giving the desired drug delivery (with minimal nasolacrymal wastage) and excellent tissue compatibility and safety for an estrogen ophthalmic in-situ gel.

DETAILED DESCRIPTION OF THE INVENTION

The present invention is an in-situ gel ophthalmic drug delivery system in which a composition for instillation in the eye contains sterile deionized water, at least one estrogen, a solubilizing or complexing agent for the estrogen, optional glycerin or more preferably mannitol, a preservative based on sorbic acid, such as without limitation potassium, calcium or sodium sorbate, optional EDTA, and 0.1-0.5% gellan gum w/v as an in-situ gel forming polymer. Gellan gum is a very good polymer gel-forming agent for use in an ophthalmic formulation, because it is anionic and otherwise benign to corneal and other eye tissues. The gellan gum also forms a gel in-situ, to hold a significant portion of the administered formulation to the cornea to promote delivery of estrogen to the lens. However, gellan gum in combination with an estrogen as a hydrophobic active agent is very difficult to formulate—the estrogen requires a solubilizing or complexing agent and then the solubilizing or complexing agent must be combined (the present inventors have determined) with a compatible preservative. More particularly, in the development of the present invention, the combination of estrogen, namely, 17β-estradiol, with sulfobutylether-β-cyclodextrin and gellan gum showed promise as a stable solution of estradiol for gel-forming ophthalmic administration, but the addition of benzododecinium bromide or other benzalkonium stabilizers typical of other pharmaceutical compositions converted the solution to a cloudy composition unacceptable for eye instillation. An important feature of the present formulation, therefore, is the use of a sorbic acid or sorbic acid based preservative in particular—such as sodium, calcium or or potassium sorbate. The choice of this preservative, and its efficacy and safety, are surprising as discussed below. Overall, then, the present composition includes: sterile deionized water; 0.001-0.025% w/v of an estrogen compound (such as without limitation 17β-estradiol, ethinyl estradiol, estrone or estriol), preferably 0.005-0.025% w/v of an estrogen compound (such as without limitation 17β-estradiol, ethinyl estradiol, estrone or estriol), and more preferably about 0.025% w/v estradiol; 0.04-4% w/v of an agent capable of solubilizing and complexing estrogen compounds, such as either 0.5-2% w/v nonionic surfactant polysorbate (a well known nonionic surfactant and emulsifier derived from polyethoxylated sorbitan and oleic acid sometimes known as polysorbate 80 or TWEEN) or 0.06-0.6% w/v cyclodextrin, or preferably about 1-2% w/v polysorbate or more preferably about 1.6% w/v polysorbate; optional 2-3% w/v glycerin or more preferably 4-5% w/v mannitol, most preferably 5% w/v mannitol; 0.1-0.4% w/v (preferably 0.2-0.3% w/v) sorbic acid or potassium, calcium or sodium sorbate as preservative, most preferably about 0.3% w/v potassium sorbate; optionally about 0.01-0.03% w/v ethylenediamine tetraacetic acid (EDTA) or disodium edetate dihydrate, although preferably at least about 0.01-0.02% w/v ethylenediamine tetraacetic acid (EDTA) or disodium edetate dihydrate and most preferably about 0.02-0.03% w/v ethylenediamine tetraacetic acid (EDTA) or disodium edetate dihydrate; and gellan gum 0.1-0.5% w/v, preferably about 0.1-0.3% w/v, most preferably about 0.3% w/v as an in-situ gel forming polymer vehicle.

The individual components of the eye composition of the present invention, as identified above, are discussed in greater detail as follows.

The present ophthalmic system includes a shelf-stable composition for instillation and the necessary containers and droppers to effect the necessary dosing, such dosing being described below. The preferred carrier of the shelf-stable composition is deionized, sterile water suitable for ophthalmic formulation and application.

Into such above-described aqueous based composition is dissolved at least one estrogen compound, including without limitation 17β-estradiol, ethinyl estradiol, estrone or estriol. The most preferred estrogen for inclusion in the present formulation is 17β-estradiol, in an amount which gives a 0.001-0.025% weight by volume ("w/v") concentration, more preferably the highest (0.025% w/v) concentration. 17β-estradiol is the preferred active agent because it is the predominant estrogen in humans. However, any estrogen can be used in the present invention for reasons which include any estrogen's ability to pass readily through mucosa and other membranes including eye membranes, particularly in optimized formulations. Because estrogen is known to help to prevent cataract onset or development, and because estrogen is able to pass through the membranes of the eye upon instillation of a formulation containing estrogen, the present in-situ gel ophthalmic composition is a beneficial way to introduce an estrogen into the area of the lens in the eye of a patient in need of such preventive treatment.

Because estrogen compounds are hydrophobic and the present ophthalmic compositions are aqueous, the estrogen must be solubilized or complexed before it can be stably incorporated into the present composition. Any solubilizing or complexing agent may be used to render the estrogen stably dissolved, but two particular agents are preferred in the practice of the invention, namely, 0.5-2% w/v nonionic surfactant polysorbate (Polysorbate 80 or TWEEN) or 0.06-0.6% w/v cyclodextrin. Polysorbate 80 is a well known nonionic surfactant and emulsifier derived from polyethoxylated sorbitan and oleic acid, and as a polymer polysorbate is well known at this writing. Cyclodextrin, particularly sulfobutylether-β-cyclodextrin, is intrinsically able to complex with an estrogen compound to render it soluble. In the most preferred embodiments of the present invention, Polysorbate 80 is used in about 1-2% w/v, preferably about 1.6%, or the sulfobutylether-β-cyclodextrin is included in the amount of about 0.06-0.6%, most preferably about 0.4% w/v.

The sorbic acid preservative of the present invention is an important constituent and contributes to the new and unexpected improvements of the present formulation. Sorbic acid preservatives include, without limitation, potassium sorbate, sodium sorbate and calcium sorbate, based on 2,4-hexadienoic acid (sorbic acid) as the salt forming compound. Sorbic Acid occurs in nature in the Rowanberries and the berries of the mountain ash, and is a widely accepted preservative in the food industries. Sorbic acid is also generally known as a constituent in eye drops but, in recent years, could well have been considered a controversial additive for an in-situ gel ophthalmic due to the relatively newly appreciated mode of action of sorbic acid as a membrane active substance rather than a classic weak acid preservative. For example, in Stratford., M. et al., "Evidence that sorbic acid does not inhibit yeast as a classic "weak acid preservative," *Letters in Applied Microbiology*, Vol. 27 No. 4, pp. 203-26 (1998), the authors explore how "sorbic acid acts as a membrane active substance rather than as a weak-acid preservative." This suggests caution to one of ordinary skill prior to including sorbic acid in any gel-forming composition designed to remain in contact with eye tissues for an extended period of time, because the membrane-active nature of sorbic acid in contrast to other non-membrane-active preservatives arguably calls its use in an ophthalmic gel in doubt, at least prior to the present invention. In fact, despite expectation to the contrary the present composition containing sorbic acid or its salts as a preservative gives excellent drug delivery, stability and tissue compatibility results. Moreover, unlike prior preservatives in the context of similar formulations, the sorbic acid preservatives are not only surprisingly beneficial and safe to the eye but beneficially do not cause any incompatibility with other excipients in the formulation.

Another important constituent of the present invention is the polymer gellan gum. Gellan gum is a polysaccharide produced by controlled fermentation of the organism *Sphingomonas elodea* and generally subjected to shear to shorten its polymer chain length and render it smooth. Many commercial versions of gellan gum exist at this writing, including Kelcogel, Phytagel and Gelrite. In microbiology, gellan gum is a substitute for agar, a gelatinous substance derived from seaweed, and gellan gum is widely accepted in the food additive industry as an emulsifier, thickener and stabilizer. In the present invention it is included in the ophthalmic composition in the amount of 0.1-0.5% w/v, preferably about 0.1-0.3% w/v and more preferably about 0.3% w/v and it is the polymer which creates an in-situ gel after the desired amount of the present composition is instilled into the eye. Because of the benign character of gellan gum and its clarity, shelf-stability and non-irritating qualities, the present composition is not intended to include any substitute polymer other than the gellan gum.

By way of context, certain excipients and additives are already known and used in ophthalmic formulations and these previously known products and formulations include, without limitation, Ultra Tears® artificial tears, Isoto-Atropine (0.5%) and Tears Naturale® artificial tears (Alcon Pharmaceuticals), Refresh® artificial tears (Allergan) and Teargel® liquid gel ophthalmic formulation (Adcock Ingram Ltd.). In particular, Teargel® is a highly viscous, clear gel designed to substitute for tear fluid. After local administration, Teargel® spreads over the conjunctiva and cornea and forms a protective film, with a film break-up time of several hours. Unlike the present composition, Teargel® contains polyacrylic acid polymer rather than the gellan gum constituent of the present invention. Whereas the present formulation is a gel designed to optimize delivery of an estrogen to the eye, Teargel® is a gel designed to substitute for tear fluid in patients experiencing "dry eye syndrome," or keratoconjunctivitis sicca, or problematic infrequent blinking as occurs in anesthesia or coma.

Finally, the remaining constituents for the present ophthalmic composition include optional 2-3% w/v glycerin or more preferably about 4-5% w/v mannitol, most preferably 5% w/v mannitol, and optionally about 0.01-0.03% w/v ethylenediamine tetraacetic acid (EDTA) or disodium edetate dihydrate but preferably at least about 0.01-0.02% w/v EDTA or disodium edetate dihydrate or more preferably about 0.02-0.03% w/v EDTA.

Dosing of the present in-situ gel ophthalmic composition is in unit dosage form and in an amount sufficient—via instillation into the conjunctival sac—to deliver 0.5-12.5, more preferably 0.5-5, micrograms of estrogen per eye per administration. The composition instilled dropwise will create drops of about 50 microliters in size. Therefore, those skilled in the art will readily formulate the present composition to deliver the desired estrogen dosage in a specified number of drops—ideally one to three drops—per administration. Eye dropper bottles and dropper tips known in the art are suitable for use in the present system.

In preparing the formulations disclosed herein, existing methods for dissolving and combining ophthalmic constituents may be used. When necessary, the solvent evaporation method may be used, such as for example when ingredients to be co-dissolved are first dissolved in a short-chain alcohol such as methanol or ethanol and combined together in alcohol solution followed by evaporation of the alcohol. The present constituents may also be admixed directly using techniques known in the art.

The following Examples are illustrative.

EXAMPLES

Example 1

A particular formulation according to the invention was prepared containing the following constituents: 0.01% w/v estradiol; 1.6% w/v polysorbate 80 (Tween 80); 0.3% Kelcogel-CGLA (gellan gum); 5% w/v mannitol; 0.3% w/v potassium sorbate and 0.03% w/v ethylene diamine tetraacetic acid (EDTA). The method of formulating these constituents was as follows. The mannitol, potassium sorbate and EDTA were weighed and transferred into a beaker containing a pre-weighed volume of millipore water to correspond to the percentages of the constituents. The Kelcogel-CGLA was then weighed and added in sequential small amounts to the beaker, with stirring, to avoid formation of any lumps. Fifteen minutes' stirring allowed the Kelcogel-CGLA polymer to hydrate. The beaker was then covered with a lid and heated to 80° C. Upon reaching 80° C. the solution was allowed to stand at that temperature for 1 minute until the solution turned clear and then was allowed to return to room temperature. During cooling, the preparation was filtered using Whatman® filter paper (42.5 mm Ø). After return of the preparation to room temperature, weight adjustment was accomplished by addition of millipore water to account for the loss of water on heating. The preparation was then sterilized by autoclaving at 121° C. and 15 psi for 15 minutes. Finally, estradiol solution in Tween 80 (polysorbate 80) was added to the preparation aseptically using a 0.22 μm sterile filter to achieve the desired drug load.

Example 2

Example 1 was repeated 9 additional times to make a full 3×3 factorial design as follows. Each of the nine formulations contained 0.01% w/v estradiol, 1.6% polysorbate, 5% mannitol and 0.3% potassium sorbate. Three each of the nine formulations contained 0.1% w/v, 0.3% w/v and 0.5% w/v Kelcogel-CGLA (gellan gum), respectively. For each three formulations containing the same amount of gellan gum, the EDTA levels were varied to include 0.02% w/v, 0.03% w/v or 0.05% w/v, respectively. Formulation techniques were used according to Example 1. All formulations were found to possess desirable formulation characteristics including pH, clarity, tonicity and drug potency. In addition, anti-microbial efficacy tests showed that preferably the maximum Kelcogel-CGLA inclusion should be 0.3% and that EDTA is apparently an important additive at at least some Kelcogel-CGLA inclusion levels to comply with the USP bacterial challenge tests. Also, it was observed that increasing the level of potassium sorbate (>0.3% w/v) or disodium EDTA (>0.05% w/v) in the in situ gel formulations containing greater than or equal to 0.5% w/v gellan gum created a preparation which was too viscous to flow as an eye instillation formulation. These test results show that the inclusion of 0.3% gellan gum and at least 0.02% w/v EDTA give eye instillation in situ gel formulations having surprisingly good stability and sterility while still providing low enough viscosity for both successful administration and gel formation in a composition that is inert to the estradiol and non-irritating to the human eye.

Example 3

Example 2 was repeated except that 0.3% w/v gellan gum and 0.001% w/v estradiol was used. At this level, the formulation sustained drug release for more than 15 hours.

Example 4

Example 2 was repeated except that 0.3% w/v gellan gum and 0.025% w/v estradiol was used. This composition when tested in vivo gave excellent drug delivery profiles.

Although the invention has been described herein with reference to particular ingredients and amounts, the invention is only to be limited insofar as is set forth in the accompanying claims.

We claim:

1. An in-situ gel ophthalmic drug delivery composition comprising: water; 0.001-0.025% w/v of an estrogen selected from the group consisting of 17β-estradiol, ethinyl estradiol, estrone and estriol; 0.04-4% w/v of a solubilizing or complexing agent; 0.3% w/v sorbic acid preservative; ethylene diamine tetraacetic acid in the amount of 0.03% w/v, 4-5% w/v mannitol and gellan gum 0.1-0.3% w/v.

2. The in-situ gel ophthalmic drug delivery composition according to claim 1, wherein said solubilizing or complexing agent is 0.5-2% w/v polysorbate.

3. The in-situ gel ophthalmic drug delivery composition according to claim 1, wherein said solubilizing or complexing agent is 0.06-0.6% w/v cyclodextrin.

4. The in-situ ophthalmic drug delivery composition according to claim 1, wherein said solubilizing or complexing agent is 0.06-0.6% w/v sulfobutylether-β-cyclodextrin.

5. The in-situ ophthalmic drug delivery composition according to claim 1, wherein 2-3% w/v glycerin is present.

6. The in-situ ophthalmic drug delivery composition according to claim 1, wherein said sorbic acid preservative is selected from the group consisting of potassium sorbate, calcium sorbate and sodium sorbate.

7. An in-situ ophthalmic drug delivery composition comprising: sterile deionized water; 0.001-0.025% w/v of an estrogen compound selected from the group consisting of 17β-estradiol, ethinyl estradiol, estrone and estriol; 0.04-4% w/v of an agent selected from the group consisting of polysorbate and cyclodextrin; 2-3% w/v glycerin or 4-5% w/v mannitol; 0.3% w/v of an additive selected from the group consisting of sorbic acid, potassium sorbate, calcium sorbate and sodium sorbate; 0.03% w/v ethylenediamine tetraacetic acid or disodium edetate dihydrate; and 0.1-0.3% w/v gellan gum.

8. An in-situ ophthalmic drug delivery composition comprising: sterile deionized water; 0.005-0.025% w/v of an estrogen compound selected from the group consisting of 17β-estradiol, ethinyl estradiol, estrone and estriol; 0.04-4% w/v of an agent selected from the group consisting of polysorbate and cyclodextrin; about 5% w/v mannitol; about 0.3% w/v potassium sorbate; 0.03% w/v ethylenediamine tetraacetic acid or disodium edetate dihydrate; and 0.1-0.3% w/v gellan gum.

9. An in-situ ophthalmic drug delivery composition comprising: sterile deionized water; 0.001% w/v 17β-estradiol; 0.04-4% w/v of an agent selected from the group consisting of polysorbate and cyclodextrin; about 5% w/v mannitol; about 0.3% potassium sorbate; 0.02-0.03% w/v ethylenediamine tetraacetic acid or disodium edetate dihydrate; and 0.3% w/v gellan gum.

10. An in-situ ophthalmic drug delivery composition comprising: sterile deionized water; 0.025% w/v 17β-estradiol; 0.04-4% w/v of an agent selected from the group consisting of polysorbate and cyclodextrin; about 5% w/v mannitol; about 0.3% potassium sorbate; 0.03% w/v ethylenediamine tetraacetic acid; and 0.3% w/v gellan gum.

* * * * *